United States Patent [19]
Tanaka et al.

[11] Patent Number: 5,998,158
[45] Date of Patent: Dec. 7, 1999

[54] GLUCOSE FREE, STABLE DRY ANALYTICAL ELEMENT FOR QUANTITATIVE ANALYSIS OF CREATINE KINASE MB ISOZYME

[75] Inventors: Hideaki Tanaka; Yoshihiko Abe; Kaoru Terashima, all of Saitama, Japan

[73] Assignee: Fuji Photo Film Co., Ltd., Kanagawa, Japan

[21] Appl. No.: 09/158,484

[22] Filed: Sep. 22, 1998

[51] Int. Cl.[6] ....................................... C12Q 1/50
[52] U.S. Cl. ................................ 435/17; 435/7.4; 435/188
[58] Field of Search ................................ 435/17, 7.1, 7.4, 435/188, 194, 805; 422/55–60

[56] References Cited

U.S. PATENT DOCUMENTS

| | | |
|---|---|---|
| 4,067,775 | 1/1978 | Wurzburg et al. . |
| 4,080,265 | 3/1978 | Antonik ........................... 195/103.5 R |
| 4,387,160 | 6/1983 | Gomez et al. ............................... 435/7 |
| 4,912,033 | 3/1990 | Ladenson et al. ........................... 435/7 |
| 5,298,406 | 3/1994 | Loyd et al. ................................ 435/17 |
| 5,804,394 | 9/1998 | Suzuki et al. ............................ 435/7.4 |

FOREIGN PATENT DOCUMENTS

| | | |
|---|---|---|
| 0200541 | 1/1978 | European Pat. Off. . |
| 0200540 | 11/1986 | European Pat. Off. . |
| 0239990 | 10/1987 | European Pat. Off. . |
| 2269080 | 11/1975 | France . |
| WO 95/17520 | 6/1995 | WIPO . |

OTHER PUBLICATIONS

Landt Y. Semi–automated Direct Colorimetric Measurement of Creatine Kinase Isoenzyme MB Activity After Extraction From Serum by Use of a CK–MB Specific Monoclonal Antibody, Clin Chem 34/3 575–581, 1988.

*Primary Examiner*—Ralph Gitomer
*Attorney, Agent, or Firm*—McAulay Nissen Goldberg Kiel & Hand, LLP

[57] ABSTRACT

A dry analytical element for quantitatively analyzing creatine kinase MB isozyme is composed of a support and a creatine kinase MB isozyme-detecting agent layer. The detecting layer contains an antibody which specifically inhibits activity of M sub-unit of creatine kinase, creatine phosphate and adenosine diphosphate which react with each other to give adenosine triphosphate in the presence of creatine kinase MB isozyme, a buffer compound which keeps the layer in the range of pH 5.5 to pH 8.5 for the formation of adenosine triphosphate, and an indicator composition which reacts with the formed adenosine triphosphate to give a spectroscopically detectable compound, said indicator composition having hexokinase, nicotinamide-adenine dinucleotide or its phosphate in an oxidized form, and glucose-6-phosphate dehydrogenase but not containing glucose in such amount as to give the spectroscopically detectable compound.

6 Claims, No Drawings

GLUCOSE FREE, STABLE DRY ANALYTICAL ELEMENT FOR QUANTITATIVE ANALYSIS OF CREATINE KINASE MB ISOZYME

FIELD OF THE INVENTION

This invention relates a dry analytical element for quantitatively analyzing creatine kinase MB isozyme.

BACKGROUND OF THE INVENTION

It is generally known that quantitative analysis of creatine kinase (CK or CPK) in blood sampled from a patient is diagnostic of creeping palsy, dermatomyositis and cardiac infarction. In creatine kinase (CK), there are three isozymes, namely, creatine kinase MM (CKMM), creatine kinase MB (CKMB) and creatine kinase BB (CKBB). These isozymes are mainly present in skeletal muscle (CKMM), cardiac muscle (CKMB), or brain and spinal cord (CKBB), respectively. When cardiac infarction occurs, CKMB in cardiac muscle comes out into blood and accordingly its content in blood increases. Therefore, it is of value for diagnosis of cardiac infarction to assay CKMB in blood.

Methods for assaying creatine kinase and/or creatine kinase MB isozyme had been studied, and a precise assaying method was established.

The method for assaying creatine kinase generally comprises the steps of preparing serum or plasma of the blood sampled from a patient, forming spectroscopically detectable species according to the enzyme activity of creatine kinase contained in the serum or plasma, and measuring the amount of the formed species to determine the content of creatine kinase.

For performing the above analytical method, the following two reaction systems are employable.

1) Reaction System 1

Creatine phosphate (CP) and adenosine diphosphate (ADP) are caused to react in the presence of creatine kinase (CK) contained in the sample (serum or plasma) to form adenosine triphosphate (ATP), while pH condition of the enzyme reaction is adjusted with a buffer working in the pH range of 5.5 to 8.5. The amount of the formed adenosine triphosphate (ATP) is proportional to that of creatine kinase (CK). The thus formed ATP is caused to react with glucose (Glu) in the presence of hexokinase (HK) to prepare glucose-6-phosphate (G6P), and then the prepared G6P is caused to react with nicotinamide adenine dinucleotide (phosphate) in an oxidized form (NAD(P)) in the presence of glucose-6-phosphate dehydrogenase (G6PDH) to produce nicotinamide adenine dinucleotide (phosphate) in a reduced form (NAD(P)H). The amount of the produced NAD(P)H is measured by a spectroscopic method and determined in accordance with the calibration curve beforehand obtained. The content of creatine kinase (CK) is determined from thus determined amount of NAD(P)H.

In order to improve accuracy of the spectroscopic measurement, NAD(P)H can be further caused to react with a tetrazolium salt to form a formazan dye and then the amount of the formazan dye is measured to determine the content of creatine kinase (CK) in the sample (Japanese Patent Provisional Publication No. 63(1988)-32499).

The reaction system 1 described above is represented by the following formulas.

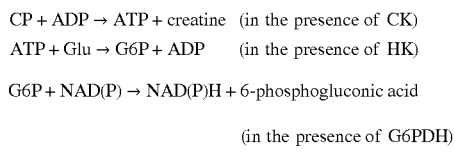

2) Reaction System 2

Creatine phosphate (CP) and adenosine diphosphate (ADP) are caused to react in the presence of creatine kinase (CK) contained in the sample to form adenosine triphosphate (ATP), while pH condition of the enzyme reaction is adjusted with a buffer working in the pH range of 5.5 to 8.5. The amount of the formed adenosine triphosphate (ATP) is proportional to that of creatine kinase (CK). The thus formed ATP is caused to react with glycerol in the presence of glycerol kinase to prepare L-α-glycerophosphate, and then the prepared L-α-glycerophosphate is caused to react with oxygen in the presence of L-α-glycerophosphate oxidase to produce hydrogen peroxide. Finally, thus produced hydrogen peroxide is caused to react with a leuco dye to form a blue dye, and then the amount of the blue dye is measured by a spectroscopic method and determined in accordance with the calibration curve beforehand obtained. The content of creatine kinase (CK) is determined from thus determined amount of the blue dye.

The reaction system 2 described above is represented by the following formulas.

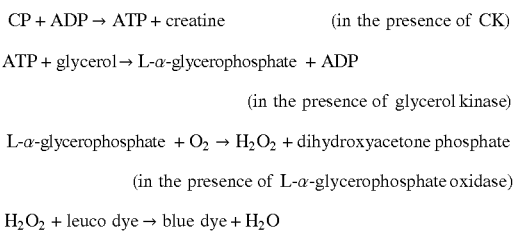

Since creatine kinase has the three isozymes described above, it is not easy to assay creatine kinase MB isozyme. Prior to assaying process, MB isozyme must be isolated from MM and BB isozymes in principle. Practically, the amount of BB isozyme in blood is negligible because it is essentially present in brain and spinal cord, but it is still very difficult to separate MB isozyme from MM isozyme.

For the purpose of obviating the above trouble, Japanese Patent Publication No. 56(1981)-19239 proposes an assaying method in which a particular antibody is employed, instead of isolating MM isozyme from the sample, to inhibit the activity of MM isozyme without adversely affecting that of MB isozyme. The antibody completely inhibits the enzyme activity of sub-unit M in MM and MB isozymes, but on the other hand it does not inhibit the activity of subunit B in MB isozyme. In the method, the sample (serum or plasma) is treated with the antibody (the M sub-unit inactivation antibody) so that creatine kinase in the sample may have only the activity originating from MB isozyme. Thereafter, thus restricted activity is measured by the above reaction system 1 or 2 to assay creatine kinase MB isozyme.

In the conventional assaying process for creatine kinase or creatine kinase MB isozyme, the reactions described above are generally performed in a solution (the process in which the reactions are performed in a solution is referred to as "wet process"). The wet process generally requires relatively long time, and accordingly it takes relatively long time to make a diagnosis based on the wet assaying process. However, for example in the case of cardiac infarction, it is needed to diagnose the case, as soon as possible, because the success of treatment depends on how soon the treatment begins. From this viewpoint, it is preferred to shorten the time to perform the assaying process.

For an assaying process which can be performed in relatively short time, a dry analytical element is known. The analytical element generally comprises a transparent support and an agent layer provided thereon which contains a reagent composition participating in the reaction system for detection. For assaying the creatine kinase MB isozyme, a dry analytical element is also developed and practically used. In the analytical element, the agent layer comprises the reagent composition for the above described reaction system 1 or 2. The detailed description about the dry analytical element for creatine kinase MB isozyme is given in the following publications; Japanese Patent Provisional Publications No. 61(1986)-254198, No. 61(1986)-254199, and No. 61(1986)-260164.

Although the dry analytical element shortens the time to perform the assaying process, the reagent composition of the analytical element is liable to deteriorate during its storage. If the analytical element is stored under ambient conditions, its sensitivity rapidly lowers. For obviating the deterioration of the reagent composition, the known dry analytical element must be stored in a refrigerator. However, it is very inconvenient to need a refrigerator for storing the analytical element, and further such inconvenience for storage often delays start of the assaying process and accordingly it often prevents an early definitive diagnosis.

Therefore, it is an object of the present invention to improve the storage stability of dry analytical element for quantitative analysis of creatine kinase MB isozyme. Particularly, it is an object of the invention to provide a isozyme dry analytical element for analysis of creatine kinase MB which does not deteriorate even if stored under ambient conditions and hence which can be stored under ambient conditions, with no need of employing a refrigerator.

SUMMARY OF THE INVENTION

The present invention resides in a dry analytical element for quantitatively analyzing creatine kinase MB isozyme comprising a support and a creatine kinase MB isozyme-detecting agent layer provided thereon, in which the layer contains an antibody which specifically inhibits activity of M sub-unit of creatine kinase, creatine phosphate and adenosine diphosphate which react with each other to give adenosine triphosphate in the presence of creatine kinase MB isozyme, a buffer compound which keeps the layer in the range of pH 5.5 to pH 8.5 for the formation of adenosine triphosphate, and an indicator composition which reacts with the formed adenosine triphosphate to give a spectroscopically detectable compound, said indicator composition comprising hexokinase, nicotinamide-adenine dinucleotide or its phosphate in an oxidized form, and glucose-6-phosphate dehydrogenase but not containing glucose in such amount as to give the spectroscopically detectable compound.

DETAILED DESCRIPTION OF THE INVENTION

According to the study made by the present inventors, it is discovered that the low storage stability of the known dry analytical element for quantitative analysis of creatine kinase MB isozyme comes from the fact that some reagents in the analytical reagent composition gradually react with each other even in the absence of the creatine kinase MB isozyme (CKMB). Particularly, in the aforementioned detective reaction system 1, CP and ADP react in part with each other in the absence of CK or CKMB to give ATP and also CP and Glu react with each other in the absence of CK or CKMB. These reactions which proceed in the absence of creatine kinase MB isozyme causes the lowering of the analytical accuracy of the dry analytical element.

In view of the above-mentioned discovery, the inventors further studied for the purpose of obviating the unfavorable side-reactions which may proceed in the dry analytical element in the storage at ambient temperatures. As a result, it has been found that the unfavorable side reactions in the analytical element utilizing the aforementioned detective reaction system 1, which may proceed in the storage, can be obviated or suppressed by removing glucose from the analytical element. In the practical analytical procedure, glucose should be present in the analytical element in order to start the detection reactions. A necessary amount of glucose, however, can be automatically incorporated into the analytical element together with a liquid sample such as serum or plasma, which is prepared from a blood containing glucose. Therefore, the removal of glucose from the dry analytical element does not disturb the quantitative analysis of CKMB isozyme.

The above-mentioned idea may be adopted for the preparation of an analytical element for quantitative analysis of creatine kinase (CK). However, since a normal test sample such as serum or plasma contains creatine kinase in an amount greater than creatine kinase MB isozyme and therefore the presence of such a greater amount of creatine kinase may produce a greater amount of ATP by catalytic reaction, the amount of glucose supplied with the test sample is not enough for accomplishing a reaction following the related reaction. Accordingly, the above-mentioned idea cannot be favorably employed in a dry analytical element utilizing the aforementioned detective reaction system 2. Moreover, the detector reagent composition according to the detective reaction system 2 does not contain any components which can be supplied with a test sample. Therefore, the idea is applicable only to the detective reaction system 1 and not to the detective reaction system 2.

The dry analytical element of the invention which has been developed for quantitative analysis of creatine kinase MB isozyme utilizes the combination of an antibody which specifically inhibits activity of M sub-unit of creatine kinase and the indicator composition according to the aforementioned detective reaction system 1 which requires glucose, and further utilizes glucose supplied with a test sample derived from a blood sample. In other words, glucose is not incorporated into the dry analytical element, or only a small amount of glucose to the extent that it causes no detectable reaction may be incorporated into the dry analytical element.

The dry analytical element of the invention utilizes the detective reaction system 1 but no or only a small amount of glucose is incorporated into the element. Therefore, the storage stability which may be lowered by glucose in the analytical element is greatly improved.

Representative examples of the analytical elements of the invention are as follows:

1) The indicator composition further comprises a tetrazolium salt.

2) The indicator composition comprises no glucose.

3) The nicotinamide-adenine dinucleotide in its oxidized dorm (NAD) is comprised in the indicator composition, and NADP is not comprised in the indicator composition.

4) The indicator composition further comprises a lactose dehydrogenase (LDH) activity-inhibiting agent.

5) The lactose dehydrogenase activity-inhibiting agent is selected from the group consisting of oxalacetic acid, oxalic acid, and oxamic acid.

In the dry analytical element of the invention, the aforementioned reaction system 1 is employed. Therefore, any indicator composition employed in the aforementioned system can be employed for the analysis utilizing the analytical element of the invention as the indicator composition which reacts with the formed adenosine triphosphate to give a spectroscopically detectable compound. Examples of the indicator composition are as follows:

1) a composition comprising hexokinase, nicotinamide-adenine dinucleotide in an oxidized form (or nicotinamide-adenine dinucleotide phosphate in an oxidized form) and glucose-6-phosphate dehydrogenase but containing no glucose or containing only a small amount of glucose; and 2) a composition comprising hexokinase, nicotinamide-adenine dinucleotide in an oxidized form (or nicotinamide-adenine dinucleotide phosphate in an oxidized form), glucose-6-phosphate dehydrogenase and a tetrazolium salt but containing no glucose or containing only a small amount of glucose.

The dry analytical element of the invention may consist of known components. The examples and detailed explanation about the components are described in the above publications, and hence no detailed descriptions on these known components are given in this specification.

Creatine phosphate (CP) and adenosine diphosphate (ADP) react with each other to form adenosine triphosphate (ATP) with the cooperation of enzyme action of creatine kinase or creatine kinase MB isozyme. It is known that the reaction should be performed in the pH range of 5.5 to 8.5. Therefore, Bis-Tris (one of Good's buffers) has been used before so as to ensure the pH condition, but at present a imidazole compound is generally employed in accordance with JSCC recommendation on creatine kinase assay.

In the analytical element of the invention, a buffer compound having a sulfonic acid group (which can be in the form of sulfonate) can be favorably employed.

The buffer compound having a sulfonic acid group preferably is one of Good's buffers. There are many compounds belonging to Good's buffers. Some of them contain a sulfonic acid group, and the others do not. A detailed description about Good's buffer is given in many known books or publications. Concrete examples of the buffer preferably employed for the invention include Good's buffers of TES, TAPSO, MOPSO, MES, DIPSO, HEPES and HEPSO. Preferred are TES, TAPSO, MOPSO and MES, and particularly preferred are TES and TAPSO.

The amount of the buffer compound is not particularly restricted, and can be easily determined by preliminary experiments beforehand performed in various amounts of the buffer compound in accordance with general usage of Good's buffer. The buffer compound which may have a sulfonic acid group can be employed singly or in combination with two or more, and further it can be also employed in combination with other buffer compound having no sulfonic acid group.

Into the detecting agent layer of the dry analytical element of the invention, a compound which can inhibit catalytic activity of LDH (lactose dehydrogenase) is preferably incorporated. According to the study made by the inventors, nicotinamide-adenine dinucleotide in its oxidized form (NAD) is favorably employed, as compared with nicotinamide-adenine dinucleotide phosphate in its oxidized form (NADP) in the dry analytical element containing no glucose or no enough amount of glucose. However, in the case of using NAD, analytical data of CKMB are apt to vary depending on the amount of LDH (lactose dehydrogenase) generally contained in a sample liquid, and therefore the analytical accuracy lowers. In order to inhibit or suppress the catalytic activity of LDH, an oxalacetic acid, oxalic acid, oxamic acid or its analogous compound is preferably incorporated into the detecting agent layer of the analytical element of the invention.

The assaying process for quantitatively analyzing creatine kinase or creatine kinase MB isozyme employing a known dry analytical element is described in the before-mentioned publications, and the assaying process using the analytical element of the invention can be also carried out in the same manner as is described therein.

The present invention is further described by the following example and comparison example.

EXAMPLE 1
[Preparation of Analytical Element for CKMB Containing No Glucose]

A transparent film of polyethylene terephthalate (thickness: 180 $\mu$m) was subjected to hydrophilic surface treatment, and then the coating solution consisting of the following components was applied onto the above-treated surface of the film. The applied solution was then dried to form a detecting agent layer having a thickness of 12 $\mu$m (in terms of thickness after dryness). The components of the coating solution for detecting agent layer are as follows:

| | |
|---|---|
| Deionized gelatin | 200 g |
| Water | 1,100 g |
| Aqueous 5% solution of nonionic surface active agent | 80 g |
| Nitrotetrazolium blue | 10 g. |

The formed detecting agent layer was wetted with a solution containing a gelatin-crosslinking agent (approx. 30 g/m$^2$), and then a sheet of tricot woven with polyethylene terephthalate yarn was compressed and fixed on the detecting agent layer. Subsequently, the sheet was dried to form a developing layer base.

On the developing layer base, the coating solution consisting of the following components was coated in an amount of 130 g/m$^2$ and then dried to form a developing layer. The components of the coating solution for developing layer are as follows:

| | |
|---|---|
| Water | 46.6 g |
| Antihuman CK-M goat antibody solution (which can inhibit more than 50% of 2000 U/L CKMM when the solution is diluted 1500 times by volume) | 20 g |
| Aqueous 10% solution of nonionic surface active agent | 2.9 g |
| Aqueous 15% solution of polyacrylamide (average molecular weight: 37,000) | 33.8 g |
| Aqueous 20% solution of magnesium chloride | 8.7 g |
| Disodium ethylenediaminetetraacetate | 0.5 g |
| Creatine phosphate (CP) | 1.3 g |
| Adensoine-5'-diphosphonic (ADP) | 0.3 g |

| | |
|---|---|
| P¹,P⁵-Di(adensosine-5'-)pentaphosphate (AP5A) | 0.25 g |
| Adenosine-5'-monophosphate (AMP) | 1.2 g |
| N-acetyl-L-cysteine | 0.1 g |
| Nicotinamide adenine dinucleotide in an axidized form (NAD) | 0.6 g |
| Oxalacetic acid | 0.07 g |
| N-tris(hydroxymethyl)methyl-2-aminoethanesulfonic acid (TES) | 5.1 g |
| 1 N NaOH | 10.0 g |
| Diaphorase | 1,500 U |
| Glucose-6-phosphate dehydrogenase | 14,000 U |
| Hexokinase (HK) | 19,400 U |
| Ascorbate oxidase | 5,000 U. |

Finally, thus prepared multi-layered composite comprising the support, the detecting agent layer and the developing layer containing the above agents was cut into pieces of 12 mm×12 mm to produce the titled analytical element. It was confirmed that most nitrotetrazolium blue having been incorporated into the detecting agent layer migrated into the developing layer of the resulting analytical element.

Comparison Example 1
[Preparation of Analytical Element for CKMB Containing Glucose]

The procedures of Example 1 were repeated except for incorporating 0.62 g of glucose into the solution to be coated on the developing layer, to prepare the titled analytical element for CKMB.
Evaluation of the Analytical Element for CKMB: Formation of ATP During Storage Each of the analytical elements produced in Example 1 and Comparison Example 1 was stored for 1 day under the conditions of 45° C. and 11% RH, and independently another fresh analytical element was prepared. Onto each of the developing layer of the stored analytical element and fresh one, a small amount of water was spotted. Subsequently, the analytical elements were incubated at 37° C. for 6 min. The spectroscopic measurement at the wavelength of 540 nm was carried out for determining coloring in the developing layer. The results are set forth in Table 1.

TABLE 1

| Analytical element | Glucose | Coloring (optical density: OD) | |
|---|---|---|---|
| | | fresh element | stored element |
| Example 1 | none | 0.50 | 0.52 |
| Com. Ex. 1 | incorporated | 0.50 | 0.61 |

The results set forth in Table 1 indicate that production of ATP in the absence of creatine kinase MB isozyme in the analytical element is effectively suppressed in the analytical element of the invention containing no glucose.

EXAMPLE 2
[Preparation of Analytical element for CKMB Containing No Glucose and No Oxalacetic Acid]

The procedures of Example 1 were repeated except for removing oxalacetic acid (whole amount) from the solution to be coated on the developing layer, to prepare the titled analytical element for CKMB.
[Evaluation of Analytical Element for Analyzing a Liquid Sample Containing LDH]

Each of the analytical elements produced in Examples 1 and 2 was stored for 10 days under the conditions of 35° C. and 11% RH. Onto each of the stored analytical element, each of two analyte samples containing the same amount of CKMB (one containing no LDH and another containing 1,000 U/L of LDH) was spotted. Subsequently, the analytical elements were incubated at 37° C. The analytical element was subjected to spectroscopic measurement at a wavelength of 540 nm after the incubation was performed for 2 min. and 5 min., to quantitatively analyze CKMB according to the reaction rate method. In the measurement, the reaction rate was determined with reference to the calibration curve beforehand obtained. The results are set forth in Table 2.

TABLE 2

| | | CKMB analysis | |
|---|---|---|---|
| Analytical element | Sample (amount of CKMB) | LDH free sample | LDH containing sample |
| Example 1 | 5 U/L | 5 U/L | 5 U/L |
| Example 2 | 5 U/L | 5 U/L | 55 U/L |

The results set forth in Table 2 indicate that an analytical element containing an LDH activity inhibitor is effective in the quantitative analysis of CKMB in a test sample which contains CKMB as well as not a small amount of lactose dehydrogenase (LDH).

What is claimed is:

1. A dry analytical element for quantitatively analyzing creatine kinase MB isozyme comprising:

a support; and
a creatine kinase MB isozyme-detecting agent layer provided thereon, said layer containing an antibody which specifically inhibits activity of the M sub-unit of creatine kinase, creatine phosphate and adenosine diphosphate which react in the presence of creatine kinase MB isozyme with each other to form adenosine triphosphate, a buffer compound which keeps the layer in the range of pH 5.5 to pH 8.5 for the formation of adenosine triphosphate, and an indicator composition which reacts with adenosine triphosphate to give a spectroscopically detectable compound;
wherein said indicator composition comprises hexokinase, nicotinamide-adenine dinucleotide or its phosphate in an oxidized form and glucose-6-phosphate dehydrogenase, and said layer contains no glucose or glucose in an insufficient amount to cause the formation of a spectroscopically detectable compound during storage of the dry analytical element.

2. The dry analytical element of claim 1, wherein the indicator composition further comprises a tetrazolium salt.

3. The dry analytical element of claim 1, wherein the layer contains no glucose.

4. The dry analytical element of claim 1, wherein the indicator composition comprises nicotinamide-adenine dinucleotide.

5. The dry analytical element of claim 1, wherein the indicator composition further comprises a lactose dehydrogenase activity-inhibiting agent.

6. The dry analytical element of claim 5, wherein the lactose dehydrogenase activity-inhibiting agent is d from the group consisting of oxalacetic acid, oxalic acid, and oxamic acid.

* * * * *